United States Patent
Takenouchi et al.

(10) Patent No.: US 10,945,592 B2
(45) Date of Patent: Mar. 16, 2021

(54) MEDICAL IMAGING APPARATUS AND ENDOSCOPE APPARATUS

(71) Applicant: Sony Olympus Medical Solutions Inc., Tokyo (JP)

(72) Inventors: Yusuke Takenouchi, Saitama (JP); Takahiro Yamamoto, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/273,237

(22) Filed: Feb. 12, 2019

(65) Prior Publication Data

US 2019/0290112 A1 Sep. 26, 2019

(30) Foreign Application Priority Data

Mar. 20, 2018 (JP) .............................. JP2018-053279

(51) Int. Cl.
| | |
|---|---|
| *A61B 1/045* | (2006.01) |
| *A61B 1/00* | (2006.01) |
| *A61B 1/05* | (2006.01) |
| *A61B 1/06* | (2006.01) |
| *G02B 23/24* | (2006.01) |

(52) U.S. Cl.
CPC .......... *A61B 1/045* (2013.01); *A61B 1/00009* (2013.01); *A61B 1/05* (2013.01); *A61B 1/0676* (2013.01); *A61B 1/00117* (2013.01); *G02B 23/2476* (2013.01)

(58) Field of Classification Search
CPC . A61B 1/00009; A61B 1/00117; A61B 1/045; A61B 1/05; A61B 1/0676; A61B 1/0002; G02B 23/2476; H04N 2005/2255
See application file for complete search history.

(56) References Cited

U.S. PATENT DOCUMENTS

| | | | | |
|---|---|---|---|---|
| 6,298,145 B1 * | 10/2001 | Zhang | ................ | G06K 9/00228 348/169 |
| 2007/0140674 A1 * | 6/2007 | Nomura | ............. | H04N 5/23248 396/52 |

(Continued)

FOREIGN PATENT DOCUMENTS

JP 2015-134039 7/2015

*Primary Examiner* — Clifford Hilaire
*Assistant Examiner* — Tyler B Edwards
(74) *Attorney, Agent, or Firm* — Xsensus, LLP

(57) ABSTRACT

A medical imaging apparatus includes an imaging unit having plural pixels each converting received light into an electric signal, thereby outputting an imaging signal; a memory to record the imaging signal; an evaluation-value calculation unit to calculate an evaluation value of an image generated from the imaging signal; an imaging signal selector to select an imaging signal to be displayed on based on the calculated evaluation value when inputting an instruction signal for selecting the imaging signal to be displayed; a memory controller to extract the selected imaging signal from the memory; and an image processing unit to process the extracted imaging signal controller to generate a display image. The evaluation-value calculation unit calculates the evaluation value by detecting the electric signal generated by each of the plural pixels included in a detection area that is a part of an effective pixel area for generating the display image.

20 Claims, 8 Drawing Sheets

(56) References Cited

U.S. PATENT DOCUMENTS

| | | | | |
|---|---|---|---|---|
| 2009/0060373 A1* | 3/2009 | Perera | ................. | G06T 5/003 |
| | | | | 382/264 |
| 2011/0298917 A1* | 12/2011 | Yanagita | ............ | H04N 5/23258 |
| | | | | 348/135 |
| 2015/0182107 A1* | 7/2015 | King | ................. | A61B 1/05 |
| | | | | 600/473 |
| 2016/0269713 A1* | 9/2016 | Kasumi | ............. | A61B 1/00193 |
| 2017/0290496 A1* | 10/2017 | Fukuda | ............... | A61B 1/0638 |

* cited by examiner

MEDICAL IMAGING APPARATUS AND ENDOSCOPE APPARATUS

CROSS-REFERENCE TO RELATED APPLICATION(S)

The present application claims priority to and incorporates by reference the entire contents of Japanese Patent Application No. 2018-053279 filed in Japan on Mar. 20, 2018.

BACKGROUND

The present invention relates to a medical imaging apparatus and an endoscope apparatus.

In the medical field, medical imaging apparatuses are known for imaging inside a living body (subject image) by using an imaging element (see, e.g., JP 2015-134039 A). A medical imaging apparatus described in JP 2015-134039 A includes a camera unit (camera head) having an imaging element mounted to an endoscope (insertion unit) inserted into a living body to capture a subject image taken by the endoscope, and a composite cable configured to transmit an imaging signal from the camera unit to a control device. Then, the control device processes the imaging signal from the medical imaging apparatus to generate a video signal for displaying and recording, and outputs the video signal to a display device or a recording device. Thus, an observation image based on the video signal is displayed on the display device or recorded in the recording device. SUMMARY Meanwhile, in order to display and record an observation image with good visibility, some medical imaging apparatuses have a function of evaluating imaging signals and displaying and recording an observation image on the basis of a result of the evaluation. Specifically, for example, shaking or blurring is detected from a video signal, and an observation image with a small amount of shaking and/or blurring is displayed and/or recorded according to the result of the detection. In recent years, along with an increase in the number of pixels of an imaging element, the data amount of imaging signal is increased, and processing time for evaluating imaging signals sequentially input is increased. As the processing time required for the evaluation increases, displaying or recording of the observation images are temporally delayed, and real-time performance in displaying the observation image or, for example, real-time performance in continuous recording, may be decreased. In addition, to efficiently evaluate an image signal having a large amount of data in a short period of time, a large-scale circuit is required.

The present disclosure is directed to a medical imaging apparatus and an endoscope apparatus.

According to a first aspect of the present disclosure, a medical imaging apparatus is provided with includes an imaging unit having a plurality of pixels each of which is configured to convert light received from an outside into an electric signal, the imaging unit outputting an imaging signal including the electric signal of each of the plurality of pixels; a memory configured to record the imaging signal generated by the imaging unit; an evaluation-value calculation unit configured to calculate an evaluation value of an image generated on the basis of the imaging signal; an imaging signal selector configured to select an imaging signal to be displayed on the basis of the evaluation value calculated by the evaluation-value calculation unit when an instruction signal for selecting the imaging signal to be displayed is input; a memory controller configured to extract the imaging signal selected by the imaging signal selector from the memory; and an image processing unit configured to process the imaging signal acquired from the memory controller to generate a display image, wherein the evaluation-value calculation unit calculates the evaluation value by detecting the electric signal generated by each of the plurality of pixels included in a detection area, and the detection area is a partial pixel area of an effective pixel area for generating the display image.

According to a second aspect of the present disclosure, a medical imaging apparatus is provided which includes an imaging unit having a plurality of pixels each of which is configured to convert light received from an outside into an electric signal, the imaging unit outputting an imaging signal including the electric signal of each of the plurality of pixels; a memory configured to record the imaging signal generated by the imaging unit; an evaluation-value calculation unit configured to calculate an evaluation value of an image generated on the basis of the imaging signal; an imaging signal selector configured to select an imaging signal to be displayed on the basis of the evaluation value calculated by the evaluation-value calculation unit when an instruction signal for selecting the imaging signal to be displayed is input; a memory controller configured to extract the imaging signal selected by the imaging signal selector from the memory; and an image processing unit configured to process the imaging signal acquired from the memory controller to generate a display image, wherein the evaluation-value calculation unit calculates the evaluation value by detecting the electric signal generated by each of the plurality of pixels included in a detection area, and the detection area represents pixel areas set according to imaging signals not overlapping each other or not adjacent to each other in acquisition time, of different imaging signals.

The above and other objects, features, advantages and technical and industrial significance of this invention will be better understood by reading the following detailed description of presently preferred embodiments of the invention, when considered in connection with the accompanying drawings.

DETAILED DESCRIPTION

Figure 1:
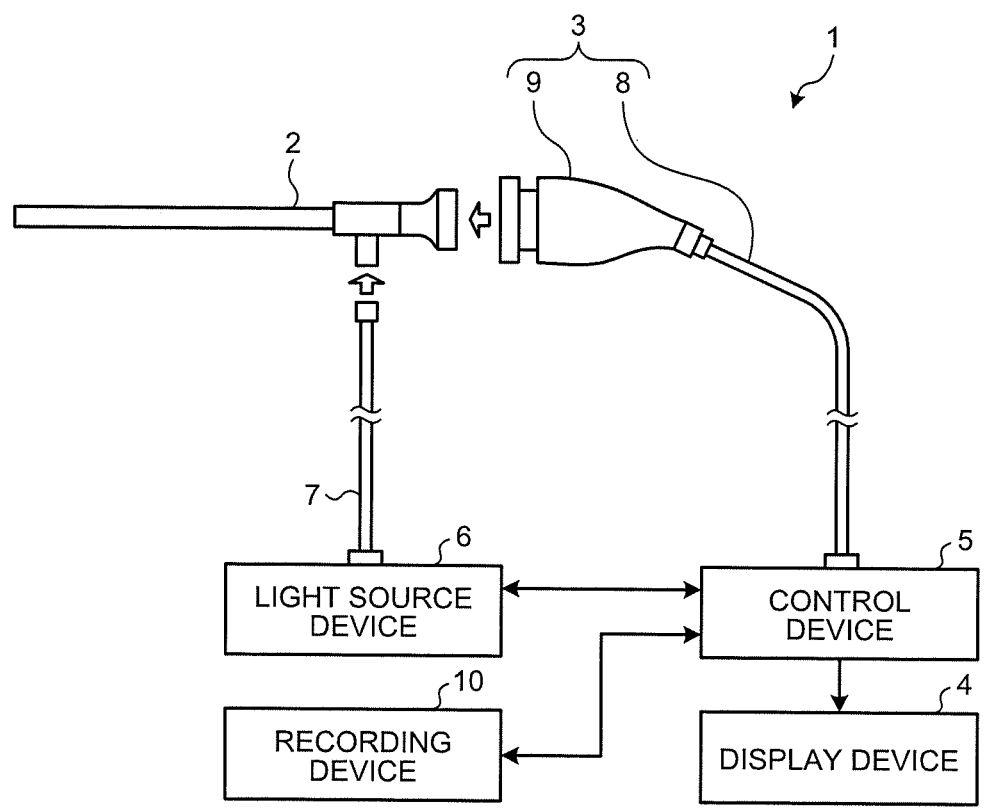
FIG. 1 is a diagram illustrating a schematic configuration of an endoscope apparatus according to an embodiment of the present invention.

Hereinafter, a mode for carrying out the present invention (hereinafter referred to as "embodiment") will be described. In the embodiments, as an example of a medical-image acquisition system including a medical imaging apparatus according to the present invention, a medical endoscope apparatus that is configured to capture and record an image in a subject, such as a patient, will be described. Furthermore, the present invention is not limited by the embodiments. Still furthermore, in the drawings, the same reference numerals are applied to the same portions, for description.

Embodiments

FIG. 1 is a diagram illustrating a schematic configuration of an endoscope apparatus 1 according to an embodiment of the present invention. The endoscope apparatus 1 is used in the medical field and is an apparatus for observing a subject inside an object to be observed (in vivo), such as a human. As illustrated in FIG. 1, the endoscope apparatus 1 includes an endoscope 2 being a rigid endoscope, an imaging device 3, a display device 4, a control device 5, a light source device 6, and a recording device 10. A medical imaging apparatus is constituted by the imaging device 3 and the control device 5.

The light source device 6 supplies white illumination light for illuminating the inside of the living body. A light guide 7 is detachably connected at one end thereof to the light source device 6 and at the other end to the endoscope 2. The light source device 6 supplies the white illumination light to the one end of the light guide 7, which then transmits the light from the one end to the other end, thereby to supply the light to the endoscope 2.

The imaging device 3 captures a subject image through the endoscope 2 and outputs the resultant captured image. As illustrated in FIG. 1, the imaging device 3 includes a transmission cable 8, which serves as a signal transmission unit, and a camera head 9.

The endoscope 2 has rigidity and an elongated shape, and is to be inserted into a living body. In the inside of the endoscope 2, an optical system is provided which includes one or a plurality of lenses to focus a subject image. The endoscope 2 emits light, which has been supplied via the light guide 7, from a distal end to irradiate the inside of the living body. Then, the light (subject image) irradiating the inside of the living body is focused by the optical system (lens unit 91) within the endoscope 2.

The camera head 9 is detachably connected to a proximal end of the endoscope 2. Then, under the control of the control device 5, the camera head 9 captures a subject image focused by the endoscope 2, and outputs an imaging signal obtained by the image capturing. A detailed configuration of the camera head 9 will be described later.

The transmission cable 8 is detachably connected at one end thereof to the control device 5 via a connector and at the other end thereof to the camera head 9 via a connector. Specifically, the transmission cable 8 is a cable in which a plurality of electric wires (not illustrated) are arranged inside an outer sheath as the outermost layer. The electric wires transmit an imaging signal output from the camera head 9 to the control device 5, and a control signal, a synchronization signal, clock, and power output from the control device 5 to the camera head 9.

Under the control of the control device 5, the display device 4 displays an image generated by the control device 5. In order for a user to concentrate on the observation of the subject, the display device 4 preferably has a display unit of 55 inch size or larger, but the display device 4 is not limited thereto.

The control device 5 processes an imaging signal input from the camera head 9 via the transmission cable 8, outputs an image signal to the display device 4 or the recording device 10, and totally controls the operation of the camera head 9, the display device 4, and the recording device 10. A detailed configuration of the control device 5 will be described later.

The recording device 10 is realized by using a semiconductor memory, such as a flash memory, a random access memory (RAM), a read only memory (ROM), or a recording medium, such as an HDD, a DVD, or a Blu-ray disc. In the recording device 10, an image signal acquired from the control device 5 is recorded. In the recording device 10, various programs and the like executed by a control unit 57 may be recorded. Incidentally, the recording device 10 may be provided in the control device 5.

Figure 2:
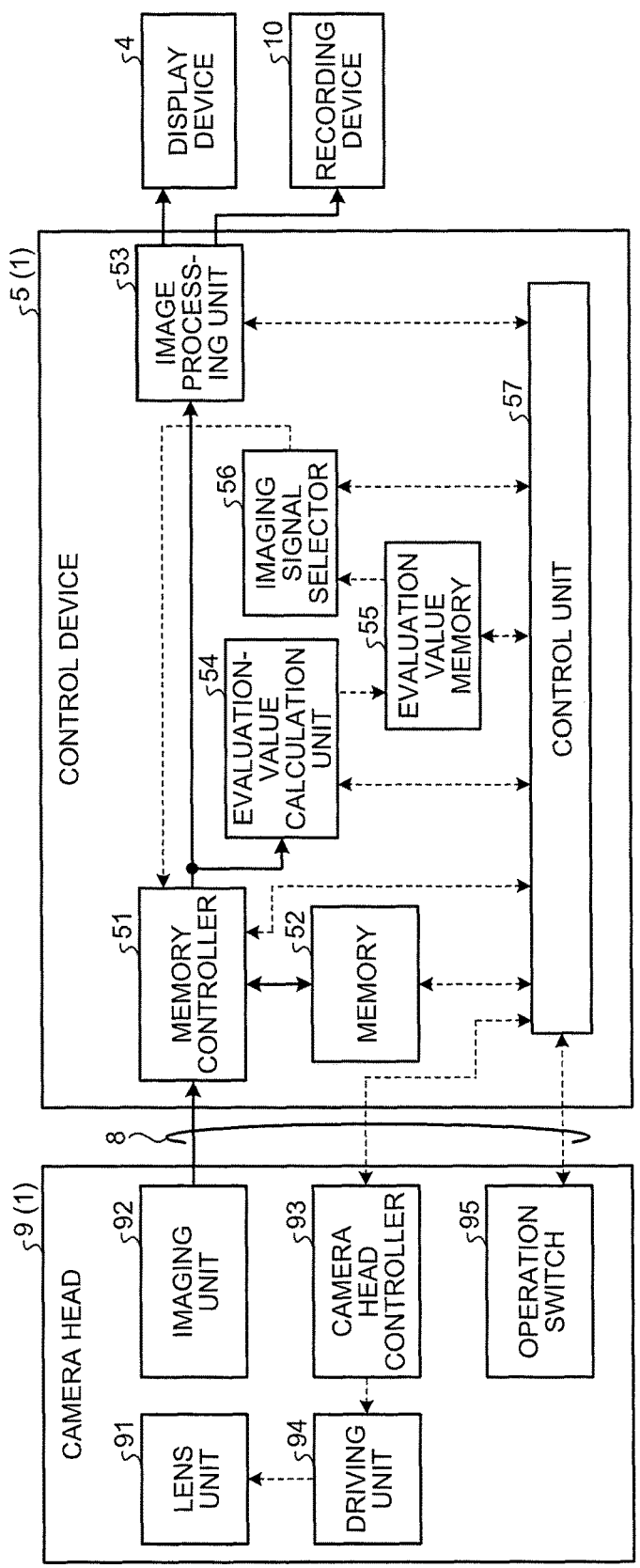
FIG. 2 is a block diagram illustrating configurations of a camera head and a control device illustrated in FIG. 1.

Next, configurations of the imaging device 3 and the control device 5 will be described. FIG. 2 is a block diagram illustrating configurations of the camera head 9 and the control device 5. In FIG. 2, a connector detachably connecting the camera head 9 and the transmission cable 8 is omitted. Furthermore, in FIG. 2, flows of signals relating to an image are indicated by solid arrows and flows of signals relating to control or the like are indicated by broken arrows.

Hereinafter, the configuration of the control device 5 and the configuration of the camera head 9 will be described in this order. In the following, as the configuration of the control device 5, main portions of the present invention will mainly be described. As illustrated in FIG. 2, the control device 5 includes a memory controller 51, a memory 52, an image processing unit 53, an evaluation-value calculation unit 54, an evaluation value memory 55, an imaging signal selector 56, and a control unit 57. Incidentally, the control device 5 may be provided with a power supply unit (not illustrated) or the like configured to generate power-supply voltage for driving the control device 5 and the camera head 9, and to supply the power-supply voltage to each unit of the control device 5 and further to the camera head 9 via the transmission cable 8.

The memory controller 51 receives an imaging signal from the camera head 9, records the imaging signal in the memory 52, and outputs the imaging signal to the evaluation-value calculation unit 54. The memory controller 51 also outputs the latest imaging signal recorded in the memory 52 or an imaging signal selected by the imaging signal selector 56 to the image processing unit 53.

The memory 52 is realized by using a semiconductor memory, such as a flash memory or a dynamic random access memory (DRAM), and records an imaging signal or communication information data (for example, communication format information etc.) acquired from the memory controller 51. Note that various programs and the like executed by the control unit 57 may be recorded in the memory 52.

The image processing unit 53 acquires an imaging signal from the memory controller 51 and performs signal processing, such as noise removal or A/D conversion as necessary on the imaging signal, to generate a digitized imaging signal (pulse signal). On the basis of the imaging signals input from the memory controller 51, the image processing unit 53 generates a display image signal to be displayed by the display device 4. The display image signal is also output to the recording device 10 so as to be recorded in the recording device 10. The image processing unit 53 performs predetermined signal processing on the imaging signal to generate the display image signal including a subject image. Here, examples of image processing include various image processing, such as interpolation, color correction, color enhancement, edge enhancement, and the like. The image processing unit 53 outputs the generated image signal to the display device 4.

Note that the image processing unit 53 may include an AF processing unit configured to output a predetermined AF evaluation value of each input frame, and an AF calculation unit configured to perform AF calculation to select a frame, a focus lens position most suitable for adjusted focus, or the like from the AF evaluation values of the respective frames output from the AF processing unit.

The evaluation-value calculation unit 54 calculates an evaluation value of an imaging signal on the basis of the imaging signal acquired from the memory controller 51. The evaluation-value calculation unit 54 calculates an evaluation value by detecting a preset detection area of an effective pixel area based on the imaging signal. The effective pixel area is a pixel area constituted by pixels generating an electric signal relating to brightness to generate an image, being part of the total pixel area constituted by all pixels.

Figure 3:
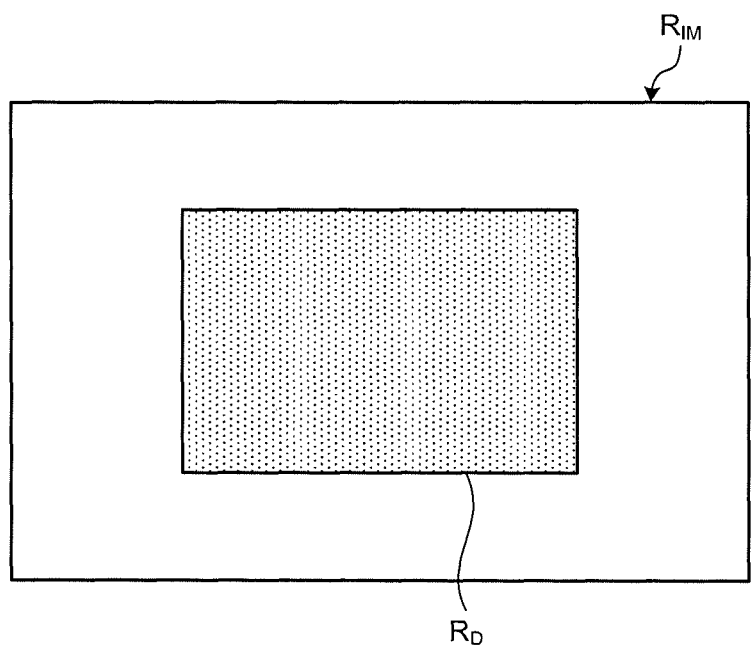
FIG. 3 is a diagram illustrating evaluation-value calculation performed by an evaluation-value calculation unit included in an endoscope apparatus according to an embodiment of the present invention.

FIG. 3 is a diagram illustrating evaluation-value calculation performed by the evaluation-value calculation unit included in the endoscope apparatus according to an embodiment of the present invention. The evaluation-value calculation unit 54 calculates an evaluation value by detecting a detection area $R_D$ set in the center portion of an effective pixel area $R_{IM}$ illustrated in FIG. 3. For example, when the number of pixels in the effective pixel area is 4400×2250, an area having 1920×1080 pixels is set for the detection area.

The evaluation-value calculation unit 54 calculates a value indicating shaking or blurring of an image as an evaluation value. Specifically, for example, the evaluation-value calculation unit 54 compares a pixel value of the detection area in an imaging signal to be detected with a pixel value of the detection area in a temporally adjacent imaging signal, and detects the shaking or blurring of an image according to the imaging signal to be detected, and obtains an amount of shaking or blurring as the evaluation value. The amount of shaking or blurring can be calculated by using a well-known method. The evaluation-value calculation unit 54 causes the calculated evaluation value to be recorded in the evaluation value memory 55.

Figure 4:
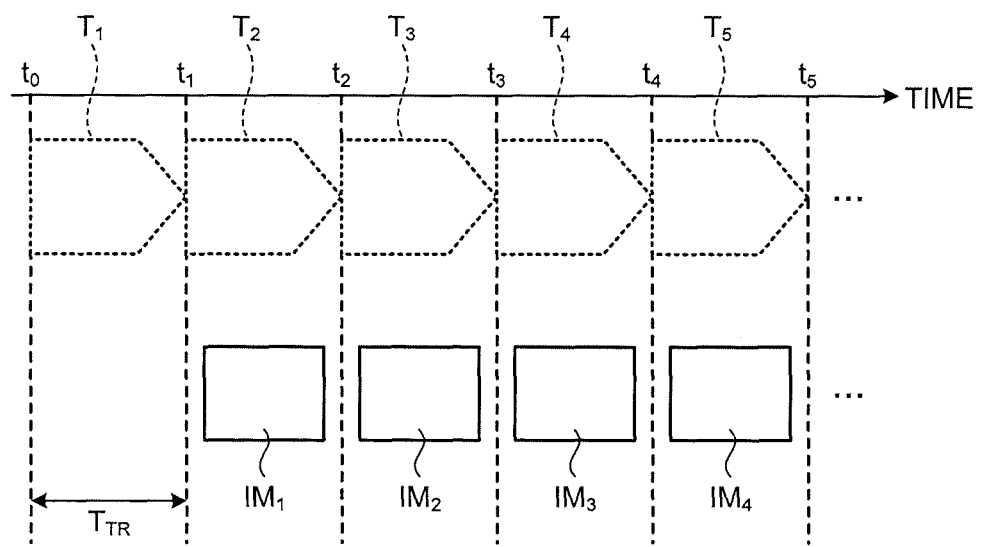
FIG. 4 is a diagram illustrating evaluation-value calculation performed by an evaluation-value calculation unit included in an endoscope apparatus according to an embodiment of the present invention.

FIG. 4 is a diagram illustrating evaluation-value calculation performed by the evaluation-value calculation unit included in the endoscope apparatus according to an embodiment of the present invention. The control device 5 generates a display image signal by the image processing unit 53 and calculates an evaluation-value by the evaluation-value calculation unit 54, on the basis of an input imaging signal. For example, imaging signals are input at time $t_0$, $t_1$, $t_2$, $t_3$, $t_4$, $t_5$, . . . , and the image processing unit 53 and the evaluation-value calculation unit 54 execute processing. Block arrows $T_1$ to $T_5$ represented by broken lines illustrated in FIG. 4 indicate periods (hereinafter referred to as evaluation-value calculation periods $T_1$ to $T_5$) each of which is required to calculate an evaluation value for one image by the evaluation-value calculation unit 54. For example, at time $t_0$, $t_1$, $t_2$ $t_5$, $t_4$, and $t_5$, temporally adjacent time intervals may be equal. Each of the evaluation-value calculation periods $T_1$ to $T_5$ is the same as an interval (interval time $T_{TR}$) between which imaging signals are input. Note that the evaluation-value calculation unit 54 desirably completes calculation of evaluation values within the respective evaluation-value calculation periods $T_1$ to $T_5$ (interval time $T_{TR}$).

By completing calculation of the evaluation values of the imaging signals within the interval time $T_{TR}$, the evaluation-value calculation unit 54 is able to continue the processing without delay for imaging signals sequentially input. Accordingly, at time at which a next imaging signal is input, an image corresponding to the latest imaging signal is displayed on the display device 4 or recorded in the recording device 10. For example, the imaging signals input at time $t_0$ are used to calculate the evaluation values within the evaluation-value calculation period $T_1$, which allows an image $IM_1$ corresponding to the imaging signals to be displayed at time $t_1$. Similarly, the imaging signals input at time $t_1$ are used to calculate evaluation values within the evaluation-value calculation period $T_2$, which allows an image $IM_2$ corresponding to the imaging signals to be displayed at time $t_2$; the imaging signals input at time $t_2$ are used to calculate evaluation values within the evaluation-value calculation period $T_2$, which allows an image $IM_3$ corresponding to the imaging signals to be displayed at time $t_3$; the imaging signals input at time $t_3$ are used to calculate evaluation values within the evaluation-value calculation period $T_4$, which allows an image $IM_4$ corresponding to the imaging signals to be displayed at time $t_4$; and the imaging signals input at time $t_4$ are used to calculate evaluation values within the evaluation-value calculation period $T_5$, which allows an image corresponding to the imaging signals to be displayed at time $t_5$. Recording to the recording device 10 is also performed in the same manner.

Recent increases in the number of pixels and resolution cause an increase in processing time. Thus, when performing the detection processing on the entire effective pixel area and calculating the evaluation values for the same area, the evaluation-value calculation unit 54 may not complete the evaluation-value calculation processing within the interval time $T_{TR}$ described above. In this case, a delay of an imaging signal corresponding to the latest evaluation value of the evaluation values recorded in the evaluation value memory 55 with respect to the latest imaging signal is increased. On the other hand, in the present embodiment, the detection area detected by the evaluation-value calculation unit 54 is defined as the detection area $R_D$ (see FIG. 3) smaller than the effective pixel area $R_{IM}$, and thereby a processing time required to calculate the evaluation values for the imaging signals is reduced, suppressing the delay in the processing time. Thus, it is possible to calculate the evaluation values up to the latest imaging signal recorded in the memory 52.

The evaluation value memory 55 is realized by using a semiconductor memory, such as a flash memory or a DRAM, and records an evaluation value calculated by the evaluation-value calculation unit 54 in association with an imaging signal. In addition, the evaluation value memory 55 outputs a recorded evaluation value in response to a request from the imaging signal selector 56. The evaluation value memory 55 may be configured to record all of the input evaluation values or record evaluation values, the number of which corresponds to a predetermined number of frames. When an upper limit is set for the number of evaluation values to be recorded and a maximum number of evaluation values are already recorded, the evaluation value memory 55 deletes the oldest evaluation value and records an evaluation value, if newly input, instead of the deleted evaluation value. As a result, the evaluation value memory 55 records a predetermined number of latest evaluation values in time order. Note that the evaluation value memory 55 may be configured as part of the memory 52.

The imaging signal selector 56 inputs, from the evaluation value memory 55, evaluation values relating to a predetermined number of imaging signals, for example the latest five frames in time order, including an evaluation value corresponding to the latest imaging signal, and extracts an evaluation value evaluated as having the smallest shaking or blurring. The imaging signal selector 56 selects an imaging signal corresponding to the extracted evaluation value, as an imaging signal to be displayed (recorded). The imaging signal selector 56 outputs selection information on the selected imaging signal to the memory controller 51. The selection information includes information specifying the selected imaging signal, such as imaging time or frame number.

The control unit 57 performs drive control of each component including the control device 5 and the camera head 9, input/output control of information to each component, and the like. The control unit 57 refers to the communication information data (for example, communication format information, etc.) recorded in the memory 52 to generate a control signal, and transmits the generated control signal to each component unit. Furthermore, the control unit 57 outputs the control signal to the camera head 9 via the transmission cable 8.

In a state where images are sequentially switched and displayed at predetermined intervals, for example, at an interval of a processing time required to generate an image on the basis of imaging signals corresponding to one frame, when a freeze instruction is input via the camera head 9, the control unit 57 causes the display device 4 to perform freeze display for displaying images at intervals longer than the above-mentioned switching intervals. At this time, in the recording device 10, recording is performed in synchronization with the displaying period.

Furthermore, the control unit 57 generates a synchronization signal and a clock for the imaging device 3 and the control device 5. A synchronization signal (for example, a synchronization signal for indicating imaging timing of the camera head 9) and a clock (for example, a clock for serial communication) to the imaging device 3 are sent to the imaging device 3 via a line (not illustrated). The imaging device 3 operates based on the synchronization signal and the clock.

The above-described memory controller 51, the image processing unit 53, the evaluation-value calculation unit 54, the imaging signal selector 56, and the control unit 57 are realized by using a general-purpose processor, such as a central processing unit (CPU), having an internal memory (not illustrated) in which a program is recorded or a dedicated processor having various arithmetic circuits, such as an application specific integrated circuit (ASIC), for performing a specific function. Furthermore, the memory controller 51, the image processing unit 53, the evaluation-value calculation unit 54, the imaging signal selector 56, and the control unit 57 may be realized by a field programmable gate array (FPGA: not illustrated) which is a type of programmable integrated circuit. When realized by the FPGA, a memory for storing configuration data may be provided so that the FPGA as the programmable integrated circuit is configured on the basis of the configuration data read from the memory.

Furthermore, the control device 5 is configured by using a user interface, such as a keyboard, mouse, or touch panel, and includes an input unit (not illustrated) configured to accept input of various information.

Next, as a configuration of the camera head 9, a main portion of the present invention will be described mainly. As illustrated in FIG. 2, the camera head 9 includes a lens unit 91, an imaging unit 92, a camera head controller 93, a driving unit 94, and an operation switch 95.

The lens unit 91 includes one or a plurality of lenses, and forms a subject image focused by the endoscope 2 on an imaging surface of an imaging element constituting the imaging unit 92. The one or the plurality of lenses are configured to be movable along the optical axis. The lens unit 91 is provided with an optical zoom mechanism (not illustrated) and a focus mechanism, in which the optical zoom mechanism changes the angle of view and the focus mechanism changes the focal point by moving the one or the plurality of lenses. In addition to the optical zoom mechanism and the focus mechanism, the lens unit 91 may be provided with a diaphragm mechanism or an optical filter (for example, a filter cutting infrared light) configured to be inserted and removed along the optical axis.

Under the control by the camera head controller 93, the imaging unit 92 images a subject. The imaging unit 92 includes the imaging element such as a charge coupled device (CCD) or a complementary metal oxide semiconductor (CMOS) configured to receive a subject image formed by the lens unit 91 on a light receiving surface including the effective pixel area in which a plurality of pixels are arranged and to convert the subject image into an electric signal. In the case of the CCD, for example, a signal processing unit (not illustrated) configured to perform signal processing (A/D conversion or the like) on an electric signal (analog signal) from the imaging element to output an imaging signal is mounted on a sensor chip or the like. In the case of CMOS, for example, a signal processing unit configured to perform signal processing (A/D conversion or the like) on an electric signal (analog) converted from light into an electric signal to output an imaging signal is included in the imaging element.

The camera head controller 93 comprehensively controls the camera head 9 according to a drive signal input via the transmission cable 8 and an instruction signal or the like output from an operating unit to an operation unit such as a switch exposed on an outer surface of the camera head 9 by the user's operation. In addition, the camera head controller 93 outputs information on a current state of the camera head 9 to the control device 5 via the transmission cable 8.

The driving unit 94 includes a driver configured to operate the optical zoom mechanism and the focus mechanism under the control of the camera head controller 93 to change the angle of view and the focal position of the lens unit 91.

The operation switch 95 includes one or more buttons, a touch panel, or the like to output an instruction signal in response to pressing of a button or a user's touch position. The operation switch 95 inputs a freeze (recording) instruction signal to the control device 5, for example, in response to pressing of a button for indicating freeze display (recording) of an image or touch operation to the touch panel.

The above-described camera head controller 93 and the driving unit 94 are realized by using a general-purpose processor, such as a CPU having an internal memory (not illustrated) in which a program is recorded or a dedicated processor having various arithmetic circuits, such as an ASIC, for performing a specific function. Furthermore, the camera head controller 93 and the driving unit 94 may include an FPGA, which is a type of a programmable integrated circuit. When the FPGA is used, a memory for storing configuration data may be provided so that the FPGA as the programmable integrated circuit is configured on the basis of the configuration data read from the memory.

Note that the camera head 9 or the transmission cable 8 may be provided with a signal processing unit configured to perform signal processing on an imaging signal generated by the imaging unit 92. Additionally, on the basis of a reference clock generated by an oscillator (not illustrated) provided in the camera head 9, an imaging clock for driving the imaging unit 92 and a driving clock for driving the driving unit 94 may be generated and output to the imaging unit 92 and the driving unit 94. Moreover, on the basis of the synchronization signal input from the control device 5 via the transmission cable 8, timing signals for various processing in the imaging unit 92, the driving unit 94, and the camera head controller 93 may be generated and output to the imaging unit 92, the driving unit 94, and the camera head controller 93. Furthermore, the camera head controller 93 may be provided in the transmission cable 8 or the control device 5 instead of at the camera head 9.

Figure 5:
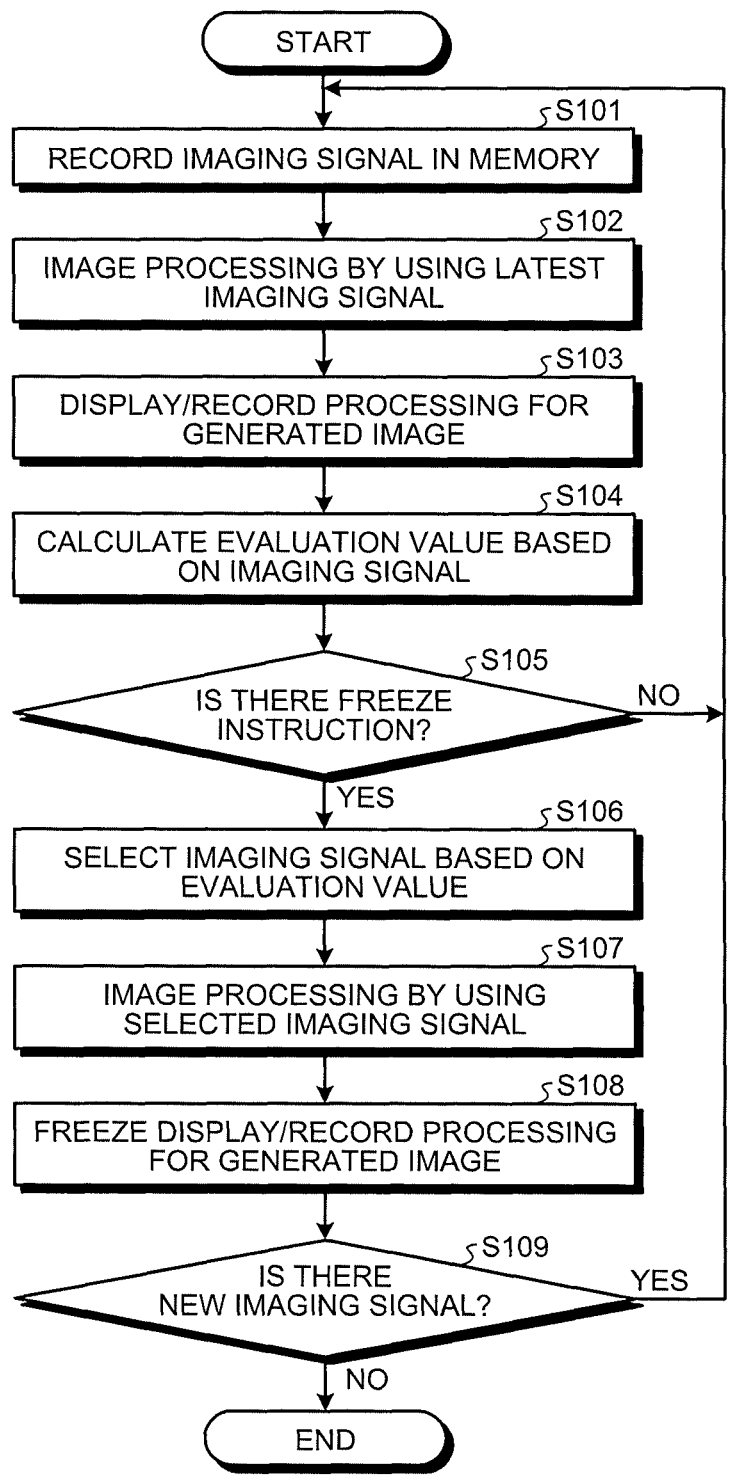
FIG. 5 is a flowchart illustrating image display processing performed by an endoscope apparatus according to an embodiment of the present invention.

Then, image display processing performed by the endoscope apparatus 1 will be described with reference to FIG. 5. FIG. 5 is a flowchart illustrating the image display processing performed by then endoscope apparatus according to an embodiment of the present invention. Hereinafter, it is assumed that each unit of the control device 5 operates under the control of the control unit 57.

When the control device 5 receives an imaging signal from the camera head 9, the memory controller 51 causes the memory 52 to record the received imaging signal (step S101). In addition, the memory controller 51 outputs the received imaging signal to the image processing unit 53 and the evaluation-value calculation unit 54. The memory controller 51 may select the imaging signal in response to the input of selection information input by the imaging signal selector 56. Here, the selection information is information indicating selection of the latest imaging signal.

Upon acquiring the latest imaging signal, the image processing unit 53 generates a display image signal (step S102). Thereafter, the image processing unit 53 outputs the generated image signal to the display device 4 and/or the recording device 10, and causes the display device 4 to display an image corresponding to the image signal or causes the recording device 10 to record the image (step S103). In step S103, images are sequentially switched and displayed (moving image display).

In step S104, the evaluation-value calculation unit 54 calculates an evaluation value by detecting a predetermined detection area (for example, see FIG. 3) of an effective pixel area based on the imaging signal acquired from the memory controller 51. The evaluation-value calculation unit 54 causes the calculated evaluation value to be recorded in the evaluation value memory 55.

Note that, as to the above-described steps S103 and S104, step S104 may be performed first or steps S103 and S104 may be performed in parallel.

In step S105, the control unit 57 determines whether a freeze instruction is input via the operation switch 95. When the control unit 57 determines that the freeze instruction is input (step S105: Yes), the control unit 57 advances the processing to step S106.

On the other hand, when the control unit 57 determines that the freeze instruction is not input (step S105: No), the control unit 57 returns the processing to step S101 and performs the above-described processing on a new input imaging signal. By repeating steps S101 to S103, images are switched and displayed on the display device 4 at predetermined intervals, for example, at an interval of a processing time required to generate an image on the basis of imaging signals corresponding to one frame. The recording device 10 is subjected to image recording processing also at the same timing.

In step S106, the imaging signal selector 56 inputs evaluation values from the evaluation value memory 55, and extracts an evaluation value evaluated as having the smallest shaking or blurring. The imaging signal selector 56 selects an imaging signal corresponding to the extracted evaluation value, as an imaging signal to be displayed (recorded). The imaging signal selector 56 outputs selection information on the selected imaging signal to the memory controller 51.

In step S107 following step S106, the memory controller 51 extracts, from the memory 52, an imaging signal corresponding to the selection information generated by the imaging signal selector 56, and outputs the imaging signal to the image processing unit 53. The image processing unit 53 processes the acquired imaging signal to generate a display image signal for freeze display (recording).

In step S108 following step S107, the control unit 57 causes the display device 4 to perform a freeze display for displaying images at intervals longer than the switching intervals used when steps S101 to S103 are repeated. At this time, the same image is recorded in the recording device 10. When a new imaging signal is input during the freeze display (recording), the evaluation-value calculation processing for the new imaging signal is performed by the evaluation-value calculation unit 54 (step S104).

According to the image processing evaluation-value calculation processing and the freeze display image selection processing as described above, an image selected from the plural images within a predetermined period or of a predetermined number that undergo the evaluation processing can be displayed as a still image on the display device for a predetermined period, when an instruction, such as the freeze instruction, is input while moving images are processed and displayed.

After the freeze display (recording) processing is completed, the control unit 57 determines whether a new imaging signal is input. When the control unit 57 determines that a new imaging signal is input (step S109: Yes), the control unit 57 returns the processing to step S101 and repeats the above-described processing. On the other hand, when the control unit 57 determines that a new imaging signal is not input (step S109: No), the control unit 57 finishes the above-described processing.

In the above-described embodiment, on the basis of an image signal obtained by performing the image processing by the image processing unit 53 on imaging signals sequentially input, the display device 4 displays an image or the recording device 10 records the image, and the evaluation-value calculation unit 54 calculates an evaluation value for evaluating shaking or blurring of the image. At this time, the evaluation-value calculation unit 54 is configured to calculate the evaluation value by detecting the detection area that is part of the effective pixel area. According to the present embodiment, even when the effective pixel area increases due to an increase in resolution, a delay in evaluation-value calculation by the evaluation-value calculation unit 54 can be suppressed and imaging signals sequentially input can be efficiently evaluated.

Note that, in the example of the above-described embodiment, one imaging signal for freeze display (recording) is selected per freeze instruction. However, the imaging signal selected is not limited to one (one frame). Selection and display (recording) of the imaging signal for freeze display (steps S106 to S108 illustrated in FIG. 5) may be repeated over a plurality of frames.

Furthermore, in the example of the above-described embodiment, the detection area is set at the center portion of the effective pixel area, but is not limited to this description. Hereinafter, another example of the detection area will be described with reference to the drawings. Modifications described below are also by way of examples, and the present invention includes all other applicable detection areas.

First Modification of Embodiment

Figure 6:
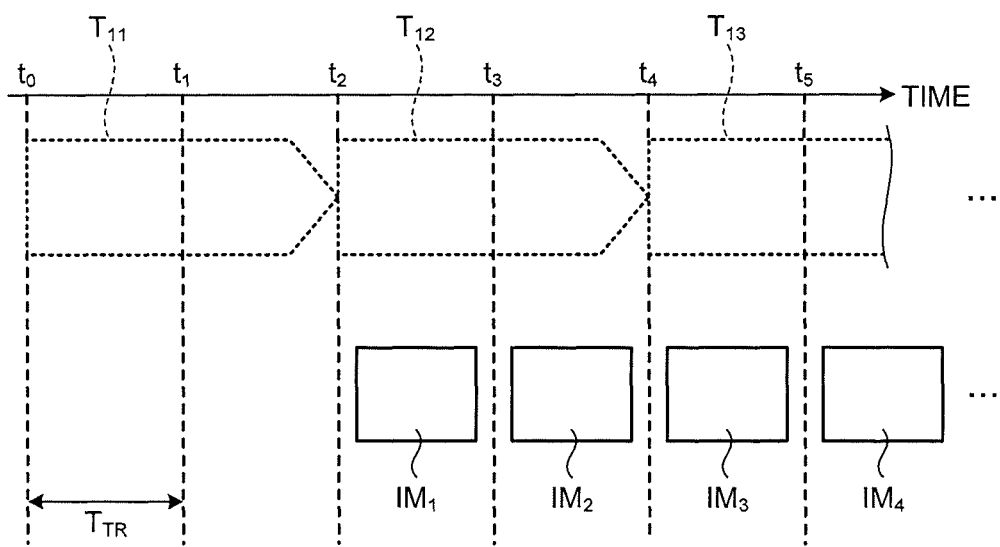
FIG. 6 is a diagram illustrating evaluation-value calculation performed by an evaluation-value calculation unit included in an endoscope apparatus according to a first modification of the embodiment of the present invention.

Next, a first modification of the embodiment of the present invention will be described. FIG. 6 is a diagram illustrating evaluation-value calculation performed by the evaluation-value calculation unit included in an endoscope apparatus according to a first modification of the embodiment of the present invention. In the first modification, the detection processing is performed with respect to images at predetermined frame intervals, and the entirety of the effective pixel area $R_{IM}$ illustrated in FIG. 3 is set as the detection area. Specifically, the detection processing is performed while decimating one frame, namely, for images $IM_1$ and $IM_3$ illustrated in FIG. 6. The detection area is the entirety of the effective pixel area $R_{IM}$. Block arrows $T_{11}$ to $T_{13}$ represented by broken lines illustrated in FIG. 6 indicate periods (evaluation-value calculation periods $T_{11}$ to $T_{13}$) each of which is required to calculate an evaluation value for one image by the evaluation-value calculation unit 54.

In the present first modification, the periods (evaluation-value calculation periods $T_{11}$ to $T_{13}$) each of which is required to calculate an evaluation value by the evaluation-value calculation unit 54 are a period (2×interval time $T_{TR}$) in which imaging signals corresponding to two frames are received. The evaluation-value calculation period $T_{11}$ is a period in which an evaluation value is calculated by using an imaging signal input at time $t_0$, from which the image $IM_1$ is generated. The evaluation-value calculation period $T_{12}$ is a period in which an evaluation value is calculated by using an imaging signal input at time $t_2$, from which the image $IM_3$ is generated. The evaluation-value calculation period $T_{13}$ is a period in which an evaluation value is calculated by using an imaging signal input at time $t_4$. As illustrated in FIG. 6, when detection processing is performed for the entirety of the effective pixel area $R_{IM}$, the detection processing cannot be completed within the interval time $T_{TR}$. However, because the detection processing is not performed for the next frame, an evaluation value can be calculated for one image over two frames. The number of frames to be decimated can be desirably set, and an interval ranging between two or more frames may be provided.

The present first modification is similar to the above-described embodiment, excluding the images (frame) that are subjected to the detection processing and the detection area to be set. When a freeze instruction is input, an image to be frozen is selected from images (here, the images $IM_1$ and $IM_3$) for which the evaluation values are calculated. According to the first modification, because an area subjected to the detection processing can be substantially reduced even when the effective pixel area increases due to an increase in resolution, a delay in evaluation-value calculation by the evaluation-value calculation unit 54 can be suppressed and imaging signals sequentially input can be efficiently evaluated.

Even in the first modification, the detection area may be set to be part of the effective pixel area $R_{IM}$ in the same manner as in the above-described embodiment. Thus, it is possible to more efficiently calculate the evaluation values, as compared with the case where all the effective pixel areas are defined as the detection area.

Furthermore, in the first modification, images for which no evaluation value is calculated (the images $IM_2$ and $IM_4$ in FIG. 6) may be associated with the evaluation values of the images of the preceding frames. For example, the evaluation value of the image $IM_2$ is associated with the evaluation value of the image $IM_1$.

Second Modification of Embodiment

Figure 7:
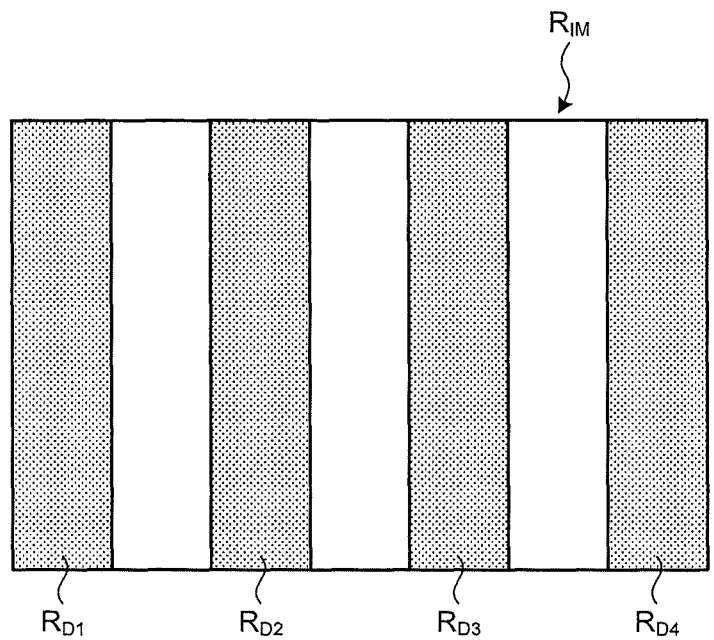
FIG. 7 is a diagram illustrating evaluation-value calculation processing according to a second modification of the embodiment of the present invention.

Next, a second modification of the embodiment of the present invention will be described. FIG. 7 is a diagram illustrating evaluation-value calculation processing according to a second modification of the embodiment of the present invention. In the second modification, detection areas including a plurality of partial detection areas (partial detection areas $R_{D1}$ to $R_{D4}$) each extending in a vertical direction in FIG. 7 are set in an effective pixel area $R_{IM}$. For example, when the effective pixel area $R_{IM}$ has 4400×2250 pixels, each of the partial detection areas $R_{D1}$ to $R_{D4}$ has an area having 630 pixels in a horizontal direction and 2250 pixels in a vertical direction, and the partial detection areas $R_{D1}$ to $R_{D4}$ are arranged at predetermined intervals.

The present second modification is similar to the above-described embodiment, excluding the detection areas to be set. In the second modification, it is possible to obtain the same effects as those of the above-described embodiment. Note that in the second modification, each of a plurality of partial detection areas extends in a vertical direction, but the partial detection area may be an area extending in a horizontal direction.

Third Modification of Embodiment

Figure 8:
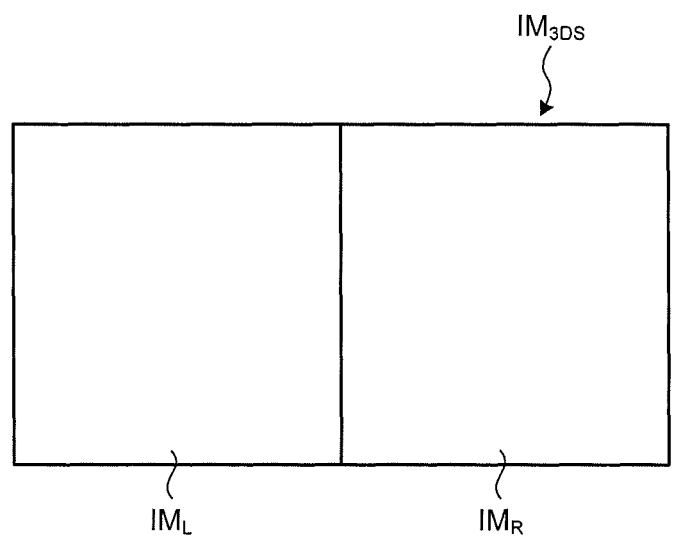
FIG. 8 is a diagram illustrating evaluation-value calculation processing according to a third modification of the embodiment of the present invention.

Next, a third modification of the embodiment of the present invention will be described. FIG. 8 is a diagram illustrating evaluation-value calculation processing according to the third modification of the embodiment of the present invention. An endoscope apparatus according to the third modification generates a stereoscopic image signal. In the present third modification, the lens unit 91 is modified to have a left-eye optical system and a right-eye optical system. The camera head 9 is modified to include the imaging unit 92 modified to generate a left-eye imaging signal and a right-eye imaging signal on the basis of light focused by the respective optical systems. The imaging unit 92 may include one imaging element having a light receiving area separated to generate the left-eye imaging signal and the right-eye imaging signal or may include two imaging elements each generating the left-eye imaging signal or the right-eye imaging signal. The left-eye imaging signal and the right-eye imaging signal are generated simultaneously or almost at the same time. The other configurations are the same as those in the embodiment described above.

An image processing unit 53 generates, as a display image signal, a three-dimensional image signal corresponding to a display method of the display device 4 or a recording method of a recording device 10, by using the left-eye imaging signal and the right-eye imaging signal. In the present third modification, the image processing unit 53 generates a side-by-side image signal. The image processing unit 53 outputs the generated three-dimensional image signal to the display device 4 or the recording device 10.

As an image $IM_{3DS}$ illustrated in FIG. 8, the side-by-side stereoscopic image includes a left-eye image $IM_L$ and a right-eye image $IM_R$, the left-eye image $IM_L$ corresponds to the left-eye imaging signals and the right-eye image $IM_R$ corresponds to the right-eye imaging signals. Here, for example, when the image $IM_{3DS}$ has 4400×2250 pixels, each of the left-eye image $IM_L$ and the right-eye image $IM_R$ has 2200×2250 pixels.

For example, the evaluation-value calculation unit 54 sets the left-eye image $IM_L$ of the image $IM_{3DS}$ as subjected to the detection processing. That is, the evaluation-value calculation unit 54 defines an area about half of the whole image $IM_{3DS}$ as a detection area. Therefore, the evaluation-value calculation unit 54 requires a processing time only about half of that in detecting the entire image $IM_{3DS}$ to calculate an evaluation value.

A memory controller 51 extracts the left-eye imaging signal selected on the basis of the evaluation value by the imaging signal selector 56 and the right-eye imaging signal corresponding to the left-eye imaging signal, and outputs the imaging signals to the image processing unit 53.

According to the third modification, because the detection area is set to about half of the image to be displayed (recorded), it is possible to obtain the same effects as those of the embodiment described above.

Fourth Modification of Embodiment

Figure 9:
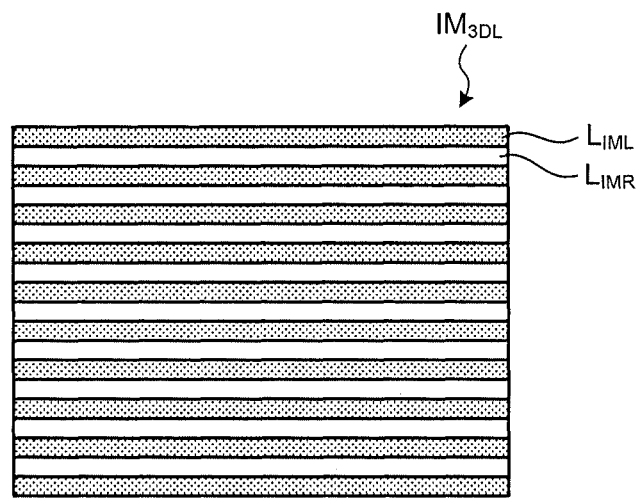
FIG. 9 is a diagram illustrating evaluation-value calculation processing according to a fourth modification of the embodiment of the present invention.

Next, a fourth modification of the embodiment of the present invention will be described. FIG. 9 is a diagram illustrating evaluation-value calculation processing according to the fourth modification of the embodiment of the present invention. An endoscope apparatus according to the fourth modification generates a stereoscopic image signal, as in the third modification.

The image processing unit 53 generates, as a display image signal, a three-dimensional image signal corresponding to a display method of the display device 4 or a recording method of the recording device 10, by using the left-eye imaging signal and the right-eye imaging signal. In the fourth modification, the image processing unit 53 generates a line-by-line image signal. The image processing unit 53 outputs the generated three-dimensional image signal to the display device 4 or the recording device 10.

As an image $IM_{3DL}$ illustrated in FIG. 9, a line-by-line stereoscopic image includes horizontal lines $L_{IML}$ and horizontal lines $L_{IMR}$ which are alternately arranged, the horizontal lines $L_{IML}$ constitute a left-eye image corresponding to the left-eye imaging signals, and the horizontal lines $L_{IMR}$ constitute a right-eye image corresponding to the right-eye imaging signals. Each horizontal line may correspond to one line in a pixel array constituting an imaging element or may correspond to a plurality of lines in the pixel array.

For example, the evaluation-value calculation unit 54 sets each horizontal line corresponding to the left-eye image of the image $IM_{3DL}$ as subjected to the detection processing. That is, the evaluation-value calculation unit 54 defines an area about half of the entire image $IM_{3DL}$ as a detection area. Therefore, the evaluation-value calculation unit 54 requires a processing time only about half of that in detecting the entire image $IM_{3DL}$ to calculate an evaluation value.

According to the fourth modification, because the detection area is set to about half of the image to be displayed (recorded), it is possible to obtain the same effects as those of the embodiment described above.

In the third and fourth modifications described above, the detection area may be further reduced by decimation. For example, when the left-eye image $IM_L$ illustrated in FIG. 8 is to be subjected to the detection processing, the center portion of the left-eye image $IM_L$ may be defined as the detection area as the detection area $R_D$ illustrated in FIG. 3, or the detection area may include decimated and divided areas, as the detection areas (partial detection areas $R_{D1}$ to $R_{D4}$) illustrated in FIG. 7.

In addition to the side-by-side stereoscopic image and the line-by-line stereoscopic image described in the third and fourth modifications described above, another stereoscopic image, such as a top-and-bottom stereoscopic image, may be used.

Fifth Modification of Embodiment

Figure 10:
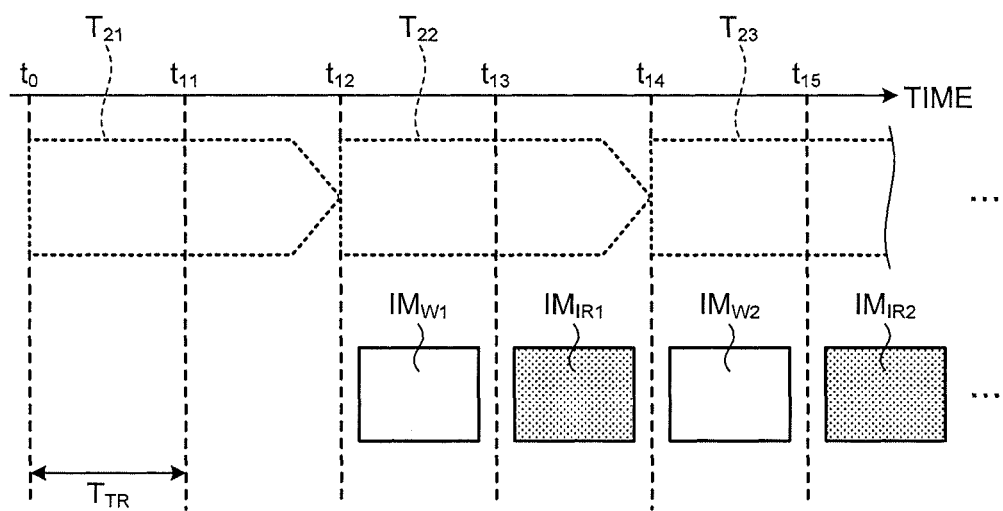
FIG. 10 is a diagram illustrating evaluation-value calculation processing according to a fifth modification of the embodiment of the present invention.

Next, a fifth modification of the embodiment of the present invention will be described. FIG. 10 is a diagram illustrating evaluation-value calculation processing according to the fifth modification of the embodiment of the present invention. An endoscope apparatus according to the fifth modification generates an image signal based on light obtained by alternately emitting illumination light having different wavelength bands. In the fifth modification, white light and infrared light including infrared wavelength light are alternately emitted. On the basis of received light, the imaging unit 92 of the camera head 9 alternately generates a white light imaging signal and an infrared imaging signal. On the basis of the white light imaging signals and the infrared imaging signals, the image processing unit 53 generates one image to be displayed (recorded). The other configurations are the same as those in the embodiment described above. Block arrows $T_{21}$ to $T_{23}$ represented by broken lines illustrated in FIG. 10 indicate periods (evaluation-value calculation periods $T_{21}$ to $T_{23}$) each of which is required to calculate an evaluation value for one image by the evaluation-value calculation unit 54.

In the fifth modification, in the control device 5, generation of a display image signal by the image processing unit 53 and calculation of an evaluation-value by the evaluation-value calculation unit 54 are performed, on the basis of an input imaging signal. For example, the white light imaging signals are input at time $t_0$, $t_{12}$, $t_{14}$, . . . , and the infrared imaging signals are input at time $t_{11}$, $t_{13}$, $t_{15}$, . . . , and the image processing unit 53 performs processing. For example, a white light image $IM_{W1}$ is generated on the basis of imaging signals input at time $t_0$. Similarly, an infrared image $IM_{IR1}$ is generated on the basis of the imaging signals input at time $t_1 1$, a white light image $IM_{W2}$ is generated on the basis of the imaging signals input at time $t1_2$, and an infrared image $IM_{IR2}$ is generated on the basis of the imaging signals input at time $t_{13}$. When the white light images and the infrared images are generated, composite images are generated by combining temporally adjacent images. For example, a composite image (not illustrated) is generated by combining the white light image $IM_{W1}$ and the infrared image $IM_{IR1}$, a composite image (not illustrated) is generated by combining the infrared image $IM_{IR1}$ and the white light image $IM_{W2}$, and a composite image (not illustrated) is generated by combining the white light image $IM_{W2}$ and the infrared image $IM_{IR2}$. Such a composite image is, for example, an image obtained by superimposing an infrared image on a white light image. In the present fifth modification, when the white light imaging signals are input (times $t_0$, $t_{12}$, $t_{14}$, . . . ), the evaluation-value calculation unit 54 calculates the evaluation values.

When a white light imaging signal is input, the evaluation-value calculation unit 54 calculates an evaluation value as described above. In this case, a detection area is the entire effective pixel area according to one of the white light imaging signals or the infrared imaging signals (here, the white light imaging signals). Here, in the fifth modification, as in the first modification, a time required to calculate evaluation values on the basis of imaging signals is a period (2×interval time $T_{TR}$) in which the imaging signals corresponding to two frames are received. Specifically, in the time chart illustrated in FIG. 10, the evaluation-value calculation period $T_{21}$ is a period in which an evaluation value is calculated by using an imaging signal input at time $t_0$, from which the white light image $IM_{W1}$ is generated. The evaluation-value calculation period $T_{22}$ is a period in which an evaluation value is calculated using the imaging signal input at time $t_{12}$, from which the white light image $T_{23}$ is generated. The evaluation-value calculation period $T_{23}$ is a period in which an evaluation value is calculated by using the imaging signal input at time $t_{14}$. For example, in the evaluation-value calculation period $T_{21}$, a time required to calculate evaluation values on the basis of the imaging signal obtained by the white light input at time $t_0$ corresponds to a processing time for two frames ranging from time $t_0$ to time $t_{12}$. The evaluation-value calculation unit 54 preferably calculates evaluation values in a time period from time $t_0$ to time $t_{12}$.

When a freeze instruction is input, a composite image to be frozen is selected on the basis of the evaluation values of white light images (here, the white light image $IM_{W1}$, the white light image $IM_{W2}$). A memory controller 51 extracts a white light imaging signal selected on the basis of the evaluation value by an imaging signal selector 56 and an infrared imaging signal corresponding to the white light imaging signal, and outputs the extracted imaging signals to the image processing unit 53. Note that when the composite images are generated in advance, the memory controller 51 extracts a composite image corresponding to a selected white light image.

In the fifth modification, although the number of evaluation values calculated is almost halved as compared with the above-described embodiments and the first to third modifications, the entire effective pixel area is defined as the detection area, and the evaluation value can be calculated highly accurately.

Here, the configuration of the imaging unit 92 according to the fifth modification will be described with reference to FIGS. 11A and 11B. The imaging unit 92 includes one imaging element configured to receive white light and infrared light or two imaging elements each configured to receive white light or infrared light.

A case where one imaging element is used

Figure 11A:
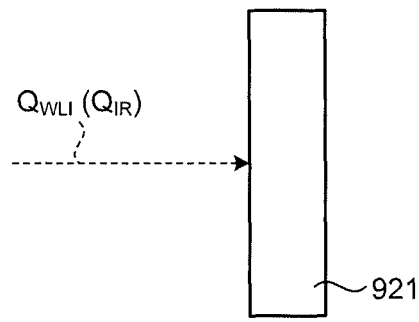
FIG. 11A is a diagram illustrating an exemplary configuration of an imaging unit included in an endoscope apparatus according to the fifth modification of the embodiment of the present invention.

FIG. 11A is a diagram illustrating an exemplary configuration of the imaging unit included in the endoscope apparatus according to the fifth modification of the embodiment of the present invention. As illustrated in FIG. 11A, when the imaging unit 92 (FIG. 2) includes one imaging element 921 configured to receive white light and infrared light, the imaging element 921 sequentially receives white light $Q_{WLI}$ and infrared light $Q_{IR}$ sequentially incident thereon and outputs an electric signal obtained by photoelectrically converting each light. This configuration has a common pixel area configured to receive the white light $Q_{WLI}$ and the infrared light $Q_{IR}$, and the same is applied to the effective pixel area.

A case where two imaging elements are used

Figure 11B:
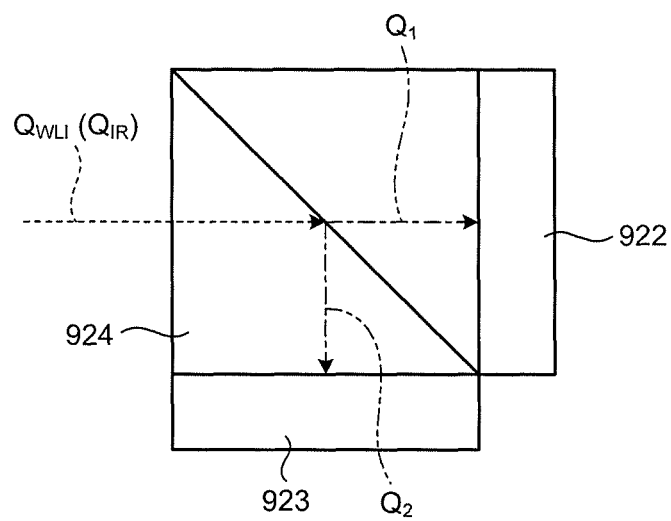
FIG. 11B is a diagram illustrating another exemplary configuration of the imaging unit included in the endoscope apparatus according to the fifth modification of the embodiment of the present invention.

FIG. 11B is a diagram illustrating another exemplary configuration of the imaging unit included in the endoscope apparatus according to the fifth modification of the embodiment of the present invention. As illustrated in FIG. 11B, when the imaging unit 92 (FIG. 2) includes two imaging elements (imaging elements 922 and 923) configured to receive white light and infrared light, respectively, a prism 924 for separating incident white light $Q_{WLI}$ and infrared light $Q_{IR}$ is provided upstream from each imaging element. The prism 924 reflects infrared wavelength light at a right angle and transmits light in a wavelength band other than the infrared wavelength band. In FIG. 11B, the imaging element 922 receives light $Q_1$ that has passed through the prism 924 and photoelectrically converts the light $Q_1$. Furthermore, the imaging element 923 receives light $Q_2$ reflected by the prism 924 and photoelectrically converts the light $Q_2$. In this configuration, the white light $Q_{WLI}$ and the infrared light $Q_{IR}$ are received by the different imaging elements, and the imaging elements have different effective pixel areas.

Figure 12:
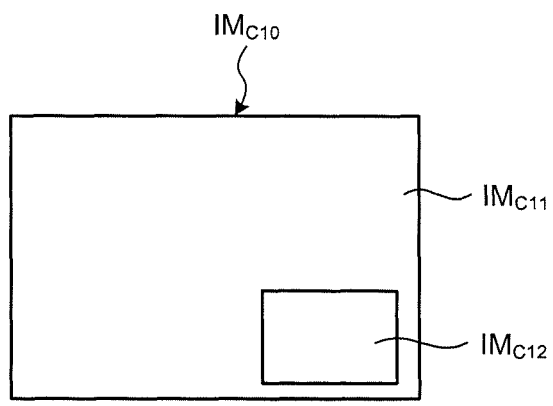
FIG. 12 is a diagram illustrating another example of an image displayed by a display device included in the endoscope apparatus according to the fifth modification of the embodiment of the present invention.

An image generated by using a white light image and an infrared image is not limited to the composite image obtained by superimposing an infrared image on a white light image as described above. FIG. 12 is a diagram illustrating another example of an image displayed on a display device included in the endoscope apparatus according to the fifth modification of the embodiment of the present invention. As a composite image $IM_{C10}$ illustrated in FIG. 12, one image may be displayed as a sub-screen on the other image. The composite image $IM_{C10}$ is an image in which an infrared image $IM_{c12}$ is superimposed in part of a white light image $IM_{C11}$. Furthermore, the white light image and the infrared image may be independently displayed.

Note that although the example using the white light imaging signal and the infrared imaging signal has been described in the present fifth modification, as long as imaging signals are obtained by light in a certain wavelength band and light in a different wavelength band, the fifth modification is applicable.

Furthermore, in the present fifth modification, the detection area may be part of the effective pixel area $R_{IM}$ in the same manner as in the above-described embodiment. This makes it possible to further suppress the delay of the evaluation-value calculation, as compared with the case of the effective pixel area wholly defined as the detection area.

Furthermore, in the fifth modification, images for which no evaluation value is calculated (the infrared image $IM_{IR1}$, the infrared image $IM_{IR2}$ in FIG. 10) may be associated with the evaluation values of the image of the preceding frames. For example, an evaluation value of the infrared image $IM_{TR1}$ are associated with an evaluation value of the white light image $IM_{W1}$.

Although the modes for carrying out the present invention have been described, the present invention should not be limited only by the embodiments described above. In the description of the above embodiments, the control device 5 performs signal processing and the like, but the camera head 9 may perform the signal processing and the like.

As described above, the medical imaging apparatus and the endoscope apparatus according to the present invention are useful to efficiently evaluate imaging signals sequentially input.

According to the present invention, it is possible to efficiently evaluate imaging signals sequentially input.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical imaging apparatus comprising:
an image sensor having a plurality of pixels each of which converts light received from an outside into an electric signal, the image sensor outputting an imaging signal including the electric signal of each of the plurality of pixels;
a memory configured to record the imaging signal output by the image sensor; and
circuitry configured to:
calculate an evaluation value of an image generated on the basis of the imaging signal by detecting the electric signal generated by each of the plurality of pixels included in a detection area;
determine a selected imaging signal to be displayed on the basis of the evaluation value in a case where an instruction signal for selecting the selected imaging signal to be displayed is input;
extract the selected imaging signal from the memory; and
process the selected imaging signal extracted from the memory to generate a display image, wherein
the detection area is a partial pixel area of an effective pixel area for generating the display image, and
the detection area further includes a first effective pixel area for a first imaging signal and a second effective pixel area for a second imaging signal, wherein the first and second effective pixel areas do not spatially overlap or are temporally delayed.

2. The medical imaging apparatus according to claim 1, wherein
the circuitry is configured to calculate the evaluation value by detecting the electric signal generated by a pixel included in the detection area among the plurality of pixels, the detection area being set by decimating the effective pixel area.

3. The medical imaging apparatus according to claim 2, wherein
the detection area is a pixel area positioned at the center of the effective pixel area.

4. The medical imaging apparatus according to claim 1, wherein
the circuitry is configured to calculate the evaluation value for evaluating a magnitude of either one or both of shaking and blurring of the image generated on the basis of the imaging signal.

5. The medical imaging apparatus according to claim 1, wherein the image sensor sequentially outputs image signals and
the circuitry is configured to:
generate display images based on the image signals,
cause a display device to display the display images at a predetermined switching interval, and
cause the display device to display one of the display images as a still image for a period of time longer than the switching interval, when a freeze instruction is input while the display images are displayed at the predetermined switching interval.

6. An endoscope apparatus comprising the medical imaging apparatus according to claim 1.

7. The medical imaging apparatus according to claim 5, wherein the image sensor detects light in an infrared region and the control circuitry is configured to, when the freeze instruction is input, output an infrared image corresponding to the selected imaging signal and to generate a composite image of the still image and the infrared image.

8. The medical imaging apparatus according to claim 1, wherein the image sensor detects light in an infrared region and the control circuitry is configured to output an infrared image corresponding to the selected imaging signal.

9. The medical imaging apparatus according to claim 1, wherein the first and second effective pixel areas do not spatially overlap or are temporally delayed by a predetermined amount.

10. The medical imaging apparatus according to claim 9, wherein the predetermined amount includes decimating at least one frame.

11. A medical imaging apparatus comprising:
an image sensor having a plurality of pixels each of which is configured to convert light received from an outside into an electric signal, the image sensor outputting an imaging signal including the electric signal of each of the plurality of pixels;
a memory configured to record the imaging signal output by the image sensor; and
circuitry configured to
calculate an evaluation value of an image output from the memory using the electric signal generated by each of the plurality of pixels included in a detection area;
determine a selected imaging signal to be displayed on the basis of the evaluation value calculated when an instruction signal for selecting the selected imaging signal to be displayed is input;
extract the selected imaging signal from the memory; and
process the imaging signal extracted from the memory to generate a display image, wherein
the detection area includes a first effective pixel area for a first imaging signal and a second effective pixel area for a second imaging signal, wherein the first and second effective pixel areas do not spatially overlap or are temporally delayed.

12. The medical imaging apparatus according to claim 11, wherein
the display image is a stereoscopic image generated on the basis of a left eye imaging signal and a right eye imaging signal, and
the circuitry is further configured to:
set as the detection area one of a first effective pixel area defined according to the left eye imaging signal and a second effective pixel area defined according to the right eye imaging signal, and
calculate the evaluation value by detecting the electric signal generated by a pixel included in the detection area among the plurality of pixels.

13. The medical imaging apparatus according to claim 11, wherein
the display image is an image generated on the basis of a first imaging signal based on light in a first wavelength band and a second imaging signal based on light in a second wavelength band different from the first wavelength band, and
the circuitry is further configured to:
use one effective pixel area of a first effective pixel area based on the first imaging signal and a second effective pixel area based on the second imaging signal as the detection area, detect the electric signal generated by a pixel included in the detection area among the plurality of pixels, and calculate the evaluation value based on the detected electrical signal.

14. The medical imaging apparatus according to claim 11, wherein circuitry is further configured to calculate the evaluation value for evaluating a magnitude of either one or both of shaking and blurring of the image generated on the basis of the imaging signal.

15. The medical imaging apparatus according to claim 11, wherein the image sensor sequentially outputs image signals and the circuitry is further configured to:

generate display images based on the image signals, cause a display device to display the display images at a predetermined switching interval, and cause the display device to display one of the display images as a still image for a period of time longer than the switching interval, when a freeze instruction is input while the display images are displayed at the predetermined switching interval.

16. An endoscope apparatus comprising the medical imaging apparatus according to claim 11.

17. The medical imaging apparatus according to claim 15, wherein the image sensor detects light in an infrared region and the control circuitry is configured to, when the freeze instruction is input, output an infrared image corresponding to the selected imaging signal and to generate a composite image of the still image and the infrared image.

18. The medical imaging apparatus according to claim 11, wherein a number of evaluation values calculated for different imaging signals over two frames is less than twice a number of the plurality of pixels.

19. The medical imaging apparatus according to claim 11, wherein the image sensor detects light in an infrared region and the control circuitry is configured to output an infrared image corresponding to the selected imaging signal.

20. The medical imaging apparatus according to claim 11, wherein the first and second effective pixel areas do not spatially overlap or are temporally delayed by a predetermined amount.

* * * * *